US007625089B2

(12) United States Patent
Youssefi et al.

(10) Patent No.: US 7,625,089 B2
(45) Date of Patent: Dec. 1, 2009

(54) WAVEFRONT SENSOR HAVING MULTI-POWER BEAM MODES, INDEPENDENT ADJUSTMENT CAMERA, AND ACCOMMODATION RANGE MEASUREMENT

(75) Inventors: Gerhard Youssefi, Landshut (DE); Hans-Joachim Polland, Wolfratshausen (DE); Christoph Sappel, Grunwald (DE)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

(21) Appl. No.: 11/369,105

(22) Filed: Mar. 6, 2006

(65) Prior Publication Data

US 2006/0152677 A1 Jul. 13, 2006

Related U.S. Application Data

(62) Division of application No. 10/110,929, filed on Mar. 13, 2003, now Pat. No. 7,036,934.

(30) Foreign Application Priority Data

| | | |
|---|---|---|
| Oct. 21, 1999 | (DE) | 199 50 792 |
| Mar. 23, 2000 | (DE) | 100 14 400 |
| Oct. 20, 2000 | (WO) | PCT/EP00/10372 |

(51) Int. Cl.
*A61B 3/10* (2006.01)

(52) U.S. Cl. ........................ 351/221; 359/205; 359/208

(58) Field of Classification Search ................. 359/246, 359/206, 209–216, 221, 232, 233, 237
See application file for complete search history.

(56) References Cited

U.S. PATENT DOCUMENTS

| | | | |
|---|---|---|---|
| 4,029,396 | A | 6/1977 | Shenker |
| 4,190,332 | A | 2/1980 | Body et al. |
| 4,471,448 | A | 9/1984 | Williams |
| 4,490,039 | A | 12/1984 | Bruckler et al. |

(Continued)

FOREIGN PATENT DOCUMENTS

| | | |
|---|---|---|
| DE | 42 22 395 A | 1/1994 |

(Continued)

OTHER PUBLICATIONS

Liang et al., *Objective measurement of wave aberrations of the human eye with the use of a Hartmann-Shack wave-front sensor*, J. Opt. Soc. Am. vol. 11, No. 7, pp. 1949-1957 (Jul. 1994).

(Continued)

*Primary Examiner*—Timothy J Thompson

(57) ABSTRACT

An improved wavefront sensor is provided that enhances the initial focus and precision of imaged spots used to determine the monochromatic wave aberrations of the eye. The wavefront sensor includes an adjustment camera that is independent of a lenslet camera. A laser in a lower power mode is projected onto the retina of the eye and is brought into more precise or sharp focus by a control system employing data from the adjustment camera, which aids in focusing the imaged spots. "Trombone"-type optics are used to adjust the focus of the light projected onto the retina and the imaged spots onto a sensor. The laser has a higher power mode used when acquiring data of the imaged spots from the sensor.

12 Claims, 11 Drawing Sheets

U.S. PATENT DOCUMENTS

| | | | | |
|---|---|---|---|---|
| 5,382,988 | A | | 1/1995 | Nanjo |
| 5,504,543 | A | | 4/1996 | Ueno |
| 5,523,809 | A | * | 6/1996 | Kohayakawa ............... 351/211 |
| 5,537,163 | A | | 7/1996 | Ueno |
| 5,684,561 | A | | 11/1997 | Yancey |
| 5,777,719 | A | | 7/1998 | Williams et al. |
| 5,891,132 | A | | 4/1999 | Hohla |
| 5,963,300 | A | | 10/1999 | Horwitz |
| 6,042,233 | A | | 3/2000 | Mihashi et al. |
| 6,155,684 | A | | 12/2000 | Bille et al. |
| 6,199,986 | B1 | | 3/2001 | Williams et al. |
| 6,264,328 | B1 | | 7/2001 | Williams et al. |
| 6,304,723 | B1 | | 10/2001 | Kohayakawa |
| 6,550,917 | B1 | | 4/2003 | Neal et al. |
| 2006/0126019 | A1 | | 6/2006 | Liang et al. |

FOREIGN PATENT DOCUMENTS

| | | | | |
|---|---|---|---|---|
| DE | 10014479 | | | 10/2001 |
| EP | 0 910 984 | A | | 4/1999 |
| JP | 11 137522 | A | | 5/1999 |
| WO | WO 93/14470 | | * | 7/1993 |
| WO | WO 93/24048 | A | | 12/1993 |
| WO | WO 96/00031 | A1 | | 1/1996 |
| WO | WO 99/27334 | | | 6/1999 |
| WO | WO 01/28476 | | | 4/2001 |

OTHER PUBLICATIONS

J. Liang and D.R. Williams, *Aberrations and retinal image quality of the normal human eye, Journal of the Optical Society of America*, vol. 14, No. 11, Nov. 1997, pp. 2873-2883.

Witthoff, C.: Wavefront Sensor Noise Reduction and Dynamic Range Expansion by Means of Optical Image Intensification:, Optical Engineering, Soc. Of Photo-Optical Instrumentation Engineers, vol. 29, No. 10, Oct. 1990 (Oct. 1990), pp. 1233-1238.

International Search Report (PCTISA/210) and Written Opinion (PCT/ISA/237) mailed on Aug. 20, 2001.

* cited by examiner

* Measurement sensitivity:

$$\theta = \frac{\Delta}{f}$$

$$W^{\infty} = W_{cornea} + W_{lens}^{\infty} \quad \text{(relaxed)}$$

$$W^{0} = W_{cornea} + W_{lens}^{0} \quad \text{(accomodated)}$$

---

$$W^{\infty} - W^{0} = W_{lens}^{\infty} - W_{lens}^{0}$$

$$W^{\infty} - W^{0} = \Delta W_{lens}$$

$$\Delta \text{Shape} = k \Delta W_{lens}$$

WAVEFRONT SENSOR HAVING MULTI-POWER BEAM MODES, INDEPENDENT ADJUSTMENT CAMERA, AND ACCOMMODATION RANGE MEASUREMENT

CROSS REFERENCE

This application is a divisional of Ser. No. 10/110,929, filed Mar. 13, 2003 now U.S. Pat. No. 7,036,934.

TECHNICAL FIELD

The invention relates to an ophthalmic wavefront aberration diagnostic tool that includes optical components that enhance its sensitivity. The invention also relates to systems using the improved tool for ophthalmic refractive surgery.

BACKGROUND ART

The field of ophthalmology for the past number of years has seen great strides in the development of refractive treatments intended to correct the vision of the eye. These techniques have evolved from the earlier radial keratotomy technique, in which slits in the cornea allowed the cornea to relax and reshape, to present techniques including photorefractive keratectomy ("PRK"), anterior lamellar keratectoiny ("ALK"), laser in situ keratomileusis ("LASIK"), and thermal techniques such as laser thermal keratoplasty ("LTK"). All of these techniques strive to provide a relatively quick but lasting correction of vision.

With the development and refinements of these techniques, greater precision has become possible in refractive error correction. In early types of treatments, the precision of the correction was relatively coarse. To provide correction to within plus or minus one diopter of the desired correction for myopia, for example, would be considered an excellent outcome. The types of treatments have become progressively refined, however, allowing more subtle defects to be corrected. Myopia and hyperopia can now be corrected to a high degree of precision with current techniques, and using excimer lasers, higher order effects can also be corrected, such as asphericity and irregular astigmatism.

At the same time, the diagnostic tools to determine what correction is needed have also advanced. Employing topography systems, vision defects can be determined and corrected irrespective of their "regularity". Such techniques are described in U.S. Pat. No. 5,891,132, entitled "Distributed Excimer Laser Surgery System," issued Apr. 6, 1999. A variety of new topography systems, pachymetry systems, wavefront sensors, and overall refractive error detection systems can detect not only the amounts of myopia, hyperopia, and astigmatism, but also, higher order aberrations of the refractive properties of the eye.

Detection of wavefront aberrations in the human eye for such purposes as intraocular surgery and contact lens and intraocular lens fabrication is disclosed, e.g., in Liang et al, "Objective measurement of wave aberrations of the human eye with the user of a Hartmann-Shack wave-front sensor," Journal of the Optical Society of America, Vol. 11, No. 7, July, 1994, pp. 1-9. That technique will be summarized with reference to FIG. 1. A beam of light from a laser diode or other suitable light source is directed toward the pupil and is incident on the retina. A beam (or wavefront, as described in FIG. 1) is reflected by the retina and emerges from the pupil. Typically, the incoming and emergent light follow a common optical path; the incoming light is brought into the common optical path with a beamsplitter. The emergent beam is applied to a Hartmann-Shack detector to detect the aberrations. Such a detector includes an array of lenslets which break up the light into an array of spots and focus the spots onto a charge-coupled detector (not shown in FIG. 1) or other two-dimensional light detector. Each spot is located to determine its displacement □ from the position which it would occupy in the absence of wavefront aberrations, and the displacements of the spots allow reconstruction of the wavefront and thus detection of the aberrations through known mathematical techniques. In FIG. 1, $\theta$ is the locally averaged wavefront slope in front of the lenslet array and is related to the spot displacement and the lenslet focal length by $\theta=\Delta/f$, as will also be appreciated by those skilled in the art.

Improvements to the technique of Liang et al are taught in J. Liang and D. R. Williams, "Aberrations and retinal image quality of the normal human eye," Journal of the Optical Society of America, Vol. 4, No. 11, November, 1997, pp. 2873-2883 and in U.S. Pat. No. 5,777,719 to Williams et al. ("Williams"). Williams teaches techniques for detecting aberrations and for using the aberrations thus detected for eye surgery and the fabrication of intraocular and contact lenses.

International Patent Publication WO 99/27334 (International App. PCT/US97/21688)("Frey") teaches a further variation using polarizing optics to control back-scatter from the lenses in the detector setup. Like Williams, Frey suggests using data from the wavefront sensor to develop an optical correction for the eye examined. More specifically, the optical correction so determined is limited to the aperture of the cornea measured by the sensor, e.g., the 6 millimeter circle to which the eye's pupil was dilated when the eye was measured. Outside that area, Frey suggests using a tapering blend zone of partial ablation to minimize severe changes in corneal curvature and hence lessen regression.

These diagnostic systems and techniques have the potential for permitting correction of both the fundamental and higher order effects, especially when used with the even more refined refractive correction techniques, with the possibility that vision correction to better than 20/20 will someday be the norm. However, improved techniques for applying advancing diagnostic technology to refractive surgery are needed.

SUMMARY OF THE INVENTION

According to the invention, a wavefront sensor can be improved by enhancing the initial focus and precision of light impinging on the retina of an eye, which aids in focusing on a sensor a group of imaged light spots that can be used to determine the higher order aberrations of the eye, generally referred to as monochromatic aberrations represented by third and higher order Zernike orders and typically excluding defocus and astigmatism. Specifically, a wavefront sensor is implemented in one embodiment with an adjustment camera independent of a lenslet camera. A laser is placed into a lower power mode and projects the light onto the retina. The light is brought into focus with the help of the adjustment camera. Because the light entering the adjustment camera that is backscattered or reflected from the retina is not divided by a lenslet array, the intensity of that light is not reduced as it would be for such a lenslet array. A control system can employ data of the light on the retina from the adjustment camera to more precisely focus the imaged spots onto the sensor using "trombone"-type focusing optics.

Once the adjustment camera has been used to initially focus the laser onto the retina, the laser is briefly brought to a higher power mode, which if left on indefinitely could damage the retina, but is only flashed for an instant. The image returned in this high power mode is then provided through the lenslet array. Although the lenslet array divides the returned light into a plurality of spots, the high power improves the signal intensity and contrast of each of those spots.

The size of the lenslet array may thus be reduced, for example, from an 800-micron center-to-center distance for the lenslets with an 80-millimeter focal length to a 400-micron center-to-center distance with a 40-millimeter focal length. This allows either a smaller footprint for the device or a greater number of lenslets and a correspondingly greater number of image points, corresponding to higher resolution of the system.

Further according to the invention, a wavefront sensor can instead employ a lenslet camera for focusing. It does so by continuously observing the centroid array from the lenslet camera and comparing the actual average centroid spacing with a perfectly focused centroid spacing. The focus of the wavefront sensor is slowly adjusted until the actual average centroid spacing is equal to the ideal focused centroid spacing, at which point it is determined that the wavefront sensor is in focus.

Further, by beginning from a myopic focus and proceeding towards a hyperopic focus, it is insured that the lens of the eye is relaxed when the wavefront sensor is brought into focus. But then by further adjusting the focus towards hyperopic, and continuing to observe the average centroid spacing, the accommodation range of an eye's lens is determined. Specifically, when the spacing of the centroid again begins to change, that is determined to be the end of the range at which the lens of the eye can accommodate for the changing focus of the wavefront sensor. This focal range determines the overall accommodation range of the lens of the eye.

Further from this data, the actual change of shape of the lens of the eye can be derived, based on the wavefronts captured when the eye first went into focus followed by when the eye went out of focus at the extent of the accommodation range of the lens.

MODE(S) FOR CARRYING OUT THE INVENTION

Figure 1:
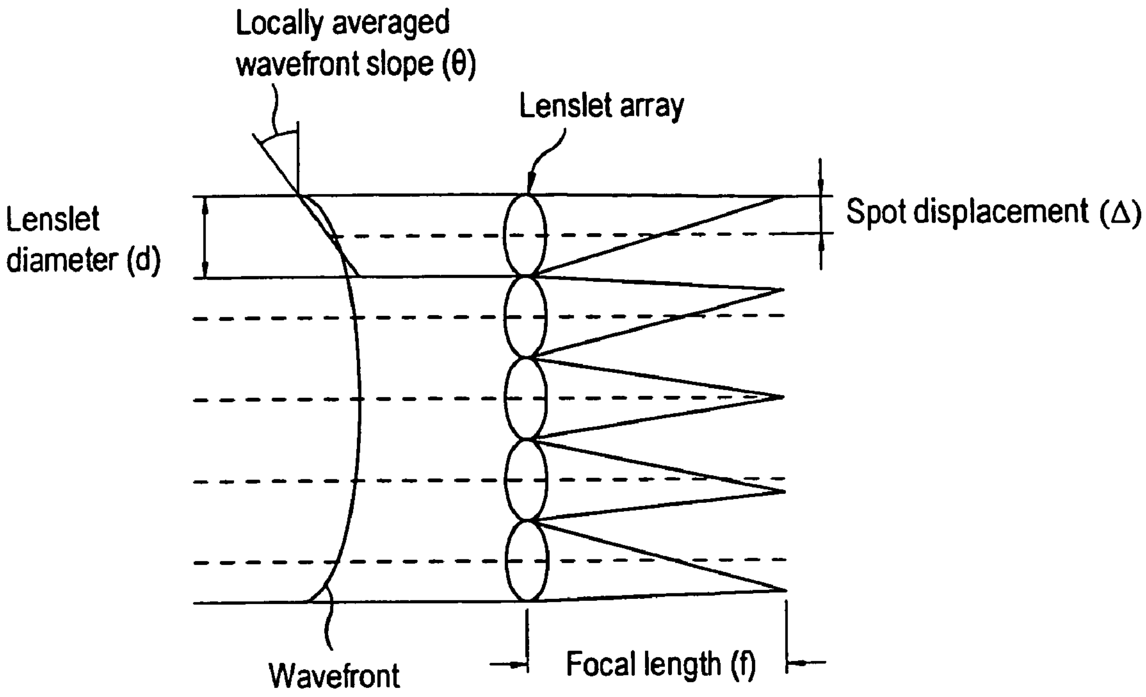
FIG. 1 illustrates principles involved in wavefront measurement.
Figure 2:
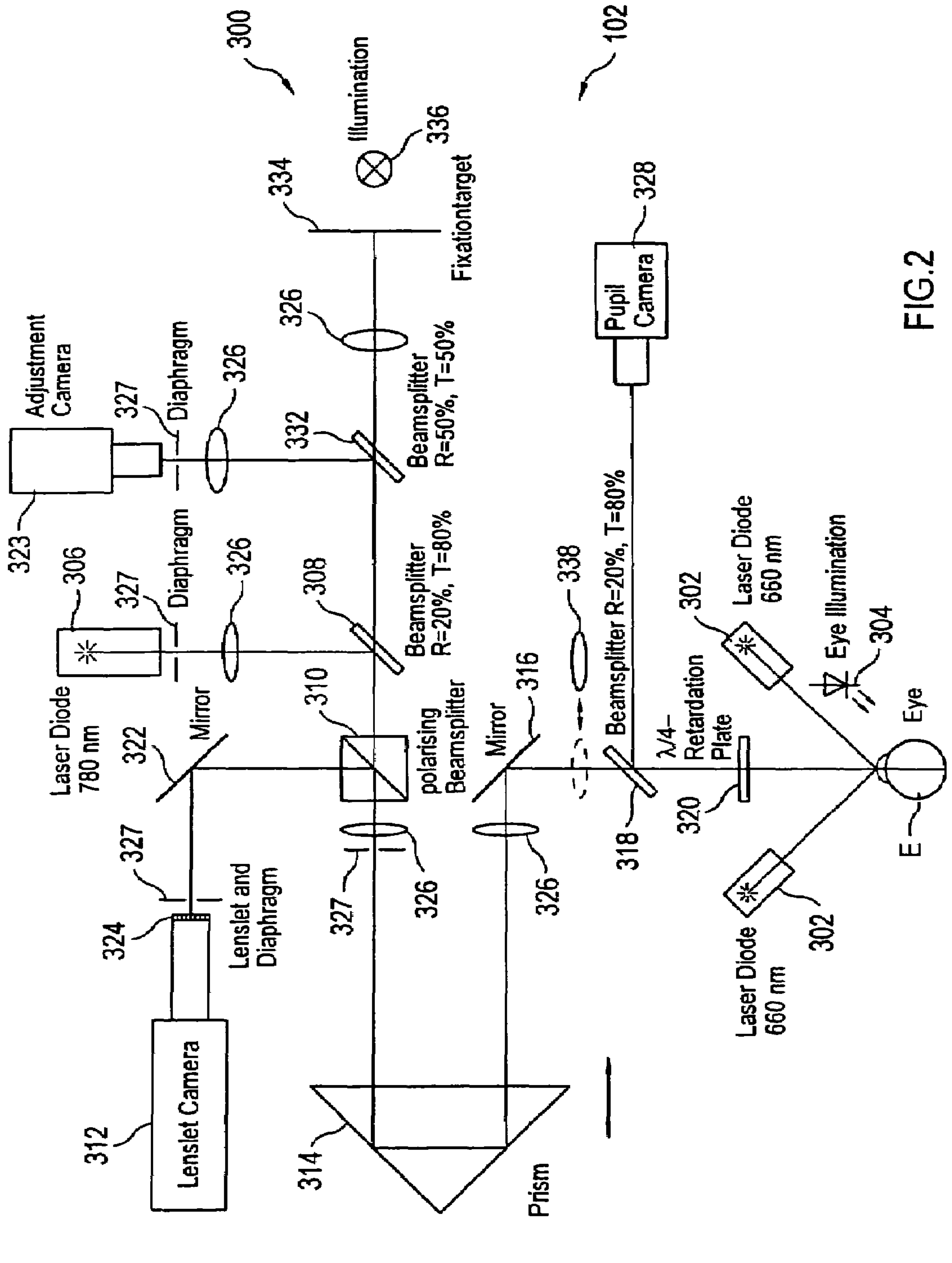
FIG. 2 is a block diagram of a wavefront sensor for use in a system according to the invention.

Turning to FIG. 2, a block diagram of a wavefront sensor 300 (Aberrometer™) is illustrated, which is a preferred implementation of this invention. The wavefront sensor 300 is similar in concept to the wavefront sensor of Williams, but includes certain features that make it especially useful for receiving iris data and for sharpening the focus of light spots on a sensor used in determining the wavefront aberrations of the eye. Further, a number of the features find general applicability to wavefront measurement devices, including those other than Williams. Such devices include scanning devices that do not have a lenslet array and multiple beam devices, e.g. Tscherning aberrometers and ray tracing aberrometers. In general, the wavefront sensor 300 focuses or scans a light (typically a laser) on the retina of an eye and then analyzes the light returned (i.e., backscattered from the retina) through the lens and corneal optics of the eye and imaged to and focused by a lenslet array. Based on optical aberrations in the eye's optics, the system develops an overall wavefront aberration analysis from the returned light. Generally, to perform the analysis, the returned light becomes aerial images formed by a lenslet array on a sensor of the lenslet camera. From these images, the wavefront sensor develops a wavefront aberration map from which can be determined what corrections are necessary to the eye's optics that would yield emmetropic, or very nearly emmetropic, vision upon correction.

To properly orient the patient's eye E, two 660-nanometer laser diodes 302, shown in FIG. 2, can be aligned at angles to the eye E. When spots on the patient's eye E from the laser diodes 302 are merged into a single spot, by appropriate adjustment of the wavefront sensor 300, the output beams of the laser diodes 302 (or optics directing these beams), the patient, or otherwise, the eye E is positioned at, or approximately at, a precise focal distance in the wavefront sensor 300. Alternatively, the patient's eye E can be properly oriented by a physician, technician, or other healthcare worker by visually looking at an iris image of the eye E to find the correct focal distance to reduce the overall exposure on the eye E. In this case, there is no need for the laser diodes 302. A light source, eye illumination 304, provides light for a pupil camera 328 discussed below.

Once the eye E is properly aligned, it receives light from a light source 306 (e.g., a laser diode, such as a 780-nanometer output laser diode) along an optical path to the eye E. Preferably, the laser diode 306 has more than one output power setting (i.e., two-power or multi-power modes), at least one at lower power for alignment and initial focusing and at least one at higher power for creation of a multi-spot image in a sensor (e.g., a lenslet camera) 312 discussed below. For example, typical lower and higher powers are 0.5 μW and 30 μW, respectively. These powers depend upon a number of factors, such as how long the laser diode 306 is to remain turned on at higher power.

A portion of the beam from the laser diode 306 first reflects from a beamsplitter 308 (e.g., 80% transmittance, 20% reflectance). The reflected beam passes through a polarizing beamsplitter 310, which ultimately improves the signal to noise ratio (or signal intensity) of light backscattered from the retina of the eye that is eventually detected by the lenslet camera 312, as discussed below. The beamsplitter 310 polarizes the light received from the laser diode 306, generally passing light linearly polarized along one direction and reflecting light not polarized in that direction. The polarized light is then passed through a trombone-assembly 314, preferably comprising one or more prisms that are translatable as a unit or one being translatable with respect to the other discussed below in conjunction with FIGS. 4A and 4B which is used to adjust the focus of the light from the laser diode 306 onto the retina of the eye E, at which point light backscattered onto the lenslet array from the light impinging on the retina will also be correctly or nearly correctly focused. The light from the trombone assembly 314 is reflected from a mirror 316, passed through a beamsplitter 318 (e.g., 20% reflectance, 80% transmittance), and then through a λ/4 waveplate 320. The λ/4 waveplate 320 is oriented to produce substantially circularly polarized light from the linearly polarized light. The significance of this will be appreciated in the discussion below of backscattered light returned (the "returned light") from the eye E to the polarizing beamsplitter 310.

After passing through the λ/4 waveplate 320, the light is then focused onto the retina of the eye E. The light is backscattered or reflected from the retina and the backscattered light spot on the retina then passes back through the optical components of the eye E, such as the lens and the cornea. On the return path, the circularly polarized image light is retarded again by the waveplate 320 to yield light linearly polarized perpendicular to the incoming linearly polarized light formed on first passage through the waveplate 320, as discussed above. A portion of the perpendicularly polarized light then passes through the beamsplitter 318, reflects from the mirror 316, passes back through the trombone assembly 314, and returns to the polarizing beamsplitter 310. At this point, all or most of the light is perpendicularly polarized, and is thus substantially reflected by the polarizing beamsplitter 310 and then reflected by a mirror 322 into the lenslet-imaging camera 312. To get some of the returned light into an adjustment camera 323, discussed further below, the waveplate 320 can be tilted and/or rotated from its optimal orientation (e.g., rotated by approximately 5 degrees). In this implementation, the light received by the adjustment camera 323 would have a polarization substantially perpendicular to the returned light. Other schemes besides tilting or rotating the waveplate 320 from its optimal orientation for providing returned light to the adjustment camera 323, including changes to the optical path and optical components of the wavefront sensor 300, are envisioned and are included within the scope of the present invention. For example, the mirror 322 instead could be a device having a controllable transmittance and reflectance, such as a liquid crystal device, and the adjustment camera and any focusing optics can be positioned to receive a fraction of the returned light that is transmitted by the controllable device. In such an implementation, the beamsplitter 308 would be unnecessary and the light received by the controllable device would have substantially the same or parallel polarization as the polarization of the returned light.

The lenslet camera 312 is preferably a charged couple device (CCD) camera, such as a TM-9701 manufactured by Pulnix, which includes an array of lenslets 324, although other types of cameras and other sampling optics analogous to the lenslet array 324 (including optics separate from a camera) could be used. For example, an ICX 039DLA camera by Sony Corporation can be used for both the lenslet camera 312 and the pupil camera 328. The lenslet array 324 forms aerial images on the light sensing element (e.g., CCD array) of the lenslet camera 312 from the returned light reflected by the mirror 322. The waveplate 320 can help to reduce the amount of unwanted backscattered or stray light to improve the signal intensity or the contrast of the aerial images. The lenslet array 324 focuses portions of the light that has initially passed through the optical components of the eye E so that the refractive wavefront aberration effects of the eye E can be determined, similar to what is disclosed in Williams. In this regard, once the wavefront aberrations, and thus phase error, of the eye E have been determined, they can be transformed to a required ablation profile for removal of corneal tissue to correct or improve vision by taking appropriate account of parameters of the eye E (e.g., the refractive indices of eye E components, and/or other parameters). One technique for determining an appropriate profile is to simply scale the wavefront data such that the scaled data generally corresponds to the amount of tissue needed to be removed from the patient's cornea. Laser systems can then remove that profile of tissue from the cornea. Marks on the eye E can be employed to aid in aligning the eye E during acquisition of wavefront sensor data.

Preferably, the lenslet array 324 is an array of approximately 25×25 lenslets, each 600 square microns, such as a 0600-40-S manufactured by Adaptive Optics Associates, Incorporated. This lenslet size is smaller than the lenslet size described in the aforementioned U.S. Pat. No. 5,777,719 patent and in other systems, and is made possible because of the enhanced intensity of light to the lenslet camera 312 provided by components of the wavefront sensor 300 to be discussed below. The optical path of the wavefront sensor 300 shown in FIG. 9 can also include lenses 326 (e.g., four lenses) and diaphragms or apertures 327 (to allow changes in beam sizes) that are typical of illumination, imaging, and focusing optics, and which also can represent other possible optical components omitted for clarity. For example, in one embodiment of the invention, the focal length of one or both of the lenses 326 about the trombone focusing prism assembly 314 can be changed, e.g., shortened, to accommodate a smaller beam width entering the lenslet array 324. In another embodiment, the range of possible dioptric measurements that can be made with the wavefront sensor 300 can be changed, for example, with appropriate selection of the lens 326 in front of the laser 306, to adjust for the natural distribution of poor eyesight in the general or a select population of patients. One way to do this is to position the lens 326 (e.g., a −5 diopter lens) in front of the laser diode 306 such that the laser beam is no longer parallel. This provides a certain offset in diopters that can be used to test the patient's eye with the wavefront sensor 300. In a nonlimiting example, the dioptric range can be modified from a symmetrical −8 to +8 diopters with a symmetrical design to an asymmetrical −13 to +3 diopters with an asymmetrical design, as will be appreciated by those skilled in the art. This can be done without changing the size of the trombone focusing prism assembly 314 (or other tuning device) and/or parameters of the optics.

Alternatively to the position of the lens 326, a lens 338 could be moved into the path to the lenslet camera 312. A number of locations within the path to the lenslet camera 312 can be employed to adjust the overall range of the captured wavefront. It will be appreciated that by employing either the lens 326 or 338 moveable into and out of position, the length of "throw" necessary for the trombone is reduced. Further, the laser diode 306 typically will have some inherent "astigmatism" of its own. This can be aligned with astigmatism typically found in a patient's eye E, again increasing the overall range of the wavefront sensor 300. Specifically, such astigmatism is aligned "with the rule" as typical patient's astigmatism is found, and the lenslet camera 312 and corresponding wavefront sensor 300 software can take into account this inherent astigmatism as providing an even greater range of determinable astigmatism.

A pupil camera 328 is shown receiving (e.g., 20% of) the reflected light from the beamsplitter 318. The pupil camera 328 preferably provides the iris image data for aligning wavefront data with other diagnostic data or with ablation profiles to be projected from a laser onto an eye. This is discussed in greater detail in copending German application No. 10014479.9 entitled Iris Recognition and Tracking for Treatment of Optical Irregularities of the Eye.

The pupil camera 328 is placed in the optical path between the eye E and the trombone focusing prism 314, which allows the pupil camera 328 to focus on the pupil and iris of the eye E, irrespective of changes in the focal length of the remainder of the system for focusing on the retina. Thus, the pupil camera 328 can develop a clear image of the surface of the eye E independent of the depth of the eye E and the corresponding distance from the retina to the iris.

Focus Adjustment Camera

The wavefront sensor 300 also includes the alignment or adjustment camera 323 that receives an image of the backscattered spot on the retina of the eye E from a beamsplitter 332 (e.g., 50% reflectance, 50% transmittance). The adjustment camera 323 is in the path of the optics that focus light on the retina of the eye E and is independent of the lenslet camera 312. The adjustment camera 323 makes it possible to precisely determine when the light spot impinging from the laser diode 306 onto the retina is in, or approximately in, focus, and thus aids in determining when the backscattered light from the retina is in, or approximately in, focus on the lenslet camera 312. With the adjustment camera 323, the spot of light on the retina can be seen, which is the ultimate source for the centroids signal (as in Williams), and can be automatically examined for when it is in sharpest focus to aid in focusing the aerial images on the lenslet camera 312 as sharply as possible. In previous systems, no adjustment camera was provided. Such systems would rely just on a lenslet camera to aid in focusing light on a retina and backscattered light on the lenslet camera. The problem with this approach is that the portion of the wavefront sampled by an individual lenslet of an n-lenslet array forms an individual spot on the camera's sensor with at most approximately 1/n of the total energy of the returned backscattered light just before entering the lenslet camera. As a result, the retina (or eye) was exposed to light energy that was maintained high unnecessarily. As can be appreciated by those skilled in the art, with the present invention, the overall exposure of the retina (or eye) can be reduced relative to these previous systems because the light energy received at the adjustment camera 323 need only approximate the light energy received at an individual lenslet of the lenslet array. The adjustment camera 323 is used to directly observe the focusing of light on the retina from the laser diode 306 while the laser diode 306 is in its lower power mode. The adjustment camera 323, as implemented, thus aids focusing the aerial images on the lenslet camera 312 as sharply as possible while the laser diode 306 is in its lower power mode as well. In so doing, account can be taken of the transmittances of the polarizing beamsplitter 310 and the beamsplitter 308, the reflectance of the beamsplitter 332, and any tilt or rotation that is introduced to the λ/4 waveplate 320 from its optimal orientation to allow a portion of the returned light to pass back to the adjustment camera 323.

As discussed above, the adjustment camera 323 is used to make sure that the spot on the retina is as sharp as possible. This means that the correct trombone assembly 314 (or 314', discussed below in reference to FIGS. 4B and 4C) settings are checked as well as patient alignment. A signal can be developed (e.g., from the adjustment camera) from these settings and alignment for a manual check or for an automatic start of patient measurements or examination. Such operation also allows for enhanced light intensity into the lenslet camera 312 only for the period of time that measurements or examination occurs, and not during the focusing and adjustment period discussed above.

In the lower power mode the laser diode 306 is placed at a power low enough to prevent damage to the retina of the eye E, such as 0.5 μW. The control system's use of the adjustment camera 323 to aid in focusing the laser diode 306 onto the retina can be accomplished in many ways. For example, the spot size on the retina can be minimized or the intensity of the spot on the retina can be maximized by adjusting the position of the trombone prism assembly 314 (or 314', discussed below in reference to FIGS. 4B and 4C) in the optical path of the captured wavefront until the spot is as small as possible. The position of the trombone prism assembly 314 (or 314') establishes a "base line" myopic or hyperopic degree of dioptric correction necessary to initially compensate for the lower order refractive optical aberration characteristics of the eye E i.e., defocus and astigmatism. Making sure that the lasers 302 are aligned at an angle that maintains an overlap of their respective spots on the retina (or other method such as manually, or by visual examination of, aligning the patient's eye) with the laser diode 306 in conjunction with adjusting the position of the trombone prism 314 (or 314') is helpful while determining the base line level of myopic or hyperopic error or correction.

Once focusing is achieved, the laser diode 306 is placed in the higher power mode for a very short period of time. For example, it may be possible to use a power of 30 μW in a spot size of 10-20 microns on the retina for a period of 400 msec. Although higher intensity could damage the retina if maintained for a prolonged period of time (e.g., more than 100 sec), such a short burst is harmless. The short burst does, however, greatly increase the intensity of the individual spots on the sensor of the lenslet camera 312, so the combination of the multi-powered laser diode 306, the adjustment camera 323, the lenslet array 342, and the lenslet camera 312 can allow for higher signal intensity or higher contrast lenslet images to be developed by the lenslet camera 312 than in other systems. The higher power laser diode 306 mode may allow the use of smaller individual cross-sectional area lenslets in the lenslet array 324 compared to other systems.

Once the lenslet camera 312 data is provided, it can be directly used via the Zernike polynomials to create the wavefront aberration data, or the wavefront aberration data can be calculated as the average of a series of exposures. For example, the system can employ five "shots" and then average either the captured data or average the corresponding Zernike data. Further, widely diverging "shots" can be discarded. In the disclosed system, preferably five "shots" are taken, and the wavefront aberration data determined as the average calculated wavefront aberration.

Fixation Target

The wavefront sensor 300 also employs an image used as a fixation target 334, as shown in FIG. 2. The fixation target 334 is illuminated by a light source 336, and allows the patient to fixate and focus while the adjustment camera 323 is focused by the prism 314 on the retina. The fixation target 334 is useful when the aerial images from the lenslet array 324 are brought into focus onto the sensor of the lenslet camera 312 by adjustment of the trombone optics 314. The system advantageously provides an image for the fixation target 334, a nonlimiting example of which is the sailboat on water illustrated in FIG. 10, and not simply a fixation point. The fixation target 334 gives the eye E and the patient's brain a picture-like or actual picture image or scene—really some object or scene being viewed by the eye E—on which to focus. Focusing the eye E with a picture-like image typically is easier to accomplish than focusing to a point. The image of the fixation target allows the eye E to focus at infinity, as if the image were far away, which can aid in eliminating or reducing the effects of eye E accommodation or rotation as the aerial images are focused or the wavefront sensor data are acquired. In other words, the image of the fixation target prevents, or helps prevent to a certain extent, the eye E from focusing at less than infinity.

Figure 3:
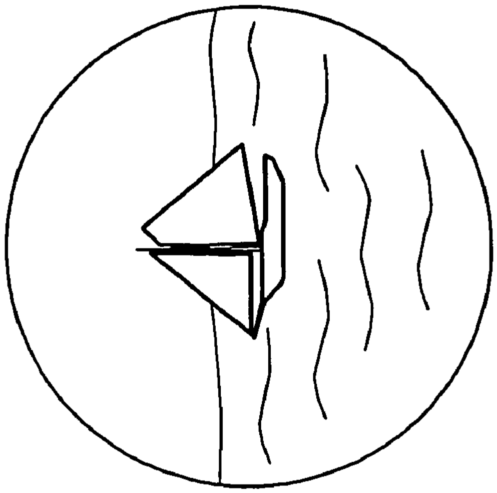
FIG. 3 is a diagram of an exemplary fixation image for use in the wavefront sensor of FIG. 2.

The fixation target image forces the eye E to rotate to its "normal" rotational position, thus minimizing rotational errors from the diagnostic analysis. Thus, with the fixation target 334, a rotational frame of reference can be defined relative to the eye E. An asymmetrical image, such as the sailboat in FIG. 3, that can be viewed at infinite eye E focus is preferable for helping the eye E maintain the normal or a pre-determined rotational position with respect to the fixation target 334, even with slight head movement. The fixation target 334 can also be used to adjust the rotational position of the eye E in conjunction with recognition, location, and alignment of an iris of the eye E, such as that described above. A similar image can be used in other components according to the present invention, both diagnostic and treatment, to eliminate or reduce accommodation or rotational issues.

It will be appreciated by those skilled in the art having the benefit of this disclosure that various types of components can be used to substitute for components implemented in the wavefront sensor 300 and various optical configurations are possible to form other embodiments of the invention. For example, a high intensity, collimated light source, or multiple light sources, for example, one low power and one high power, can replace the laser diode 306. The adjustment camera 323 can instead be placed in the path of the mirror 322, and the lenslet array 324 of the lenslet camera 312 can have more or fewer lenslets, as desired or according to design. Further, it will be appreciated by those skilled in the art that all of these components are generally controlled by a control system, such as a microcomputer. A wide variety of other configurations are possible that are within the scope and spirit of the present invention.

Focusing Prism

Figure 4A:
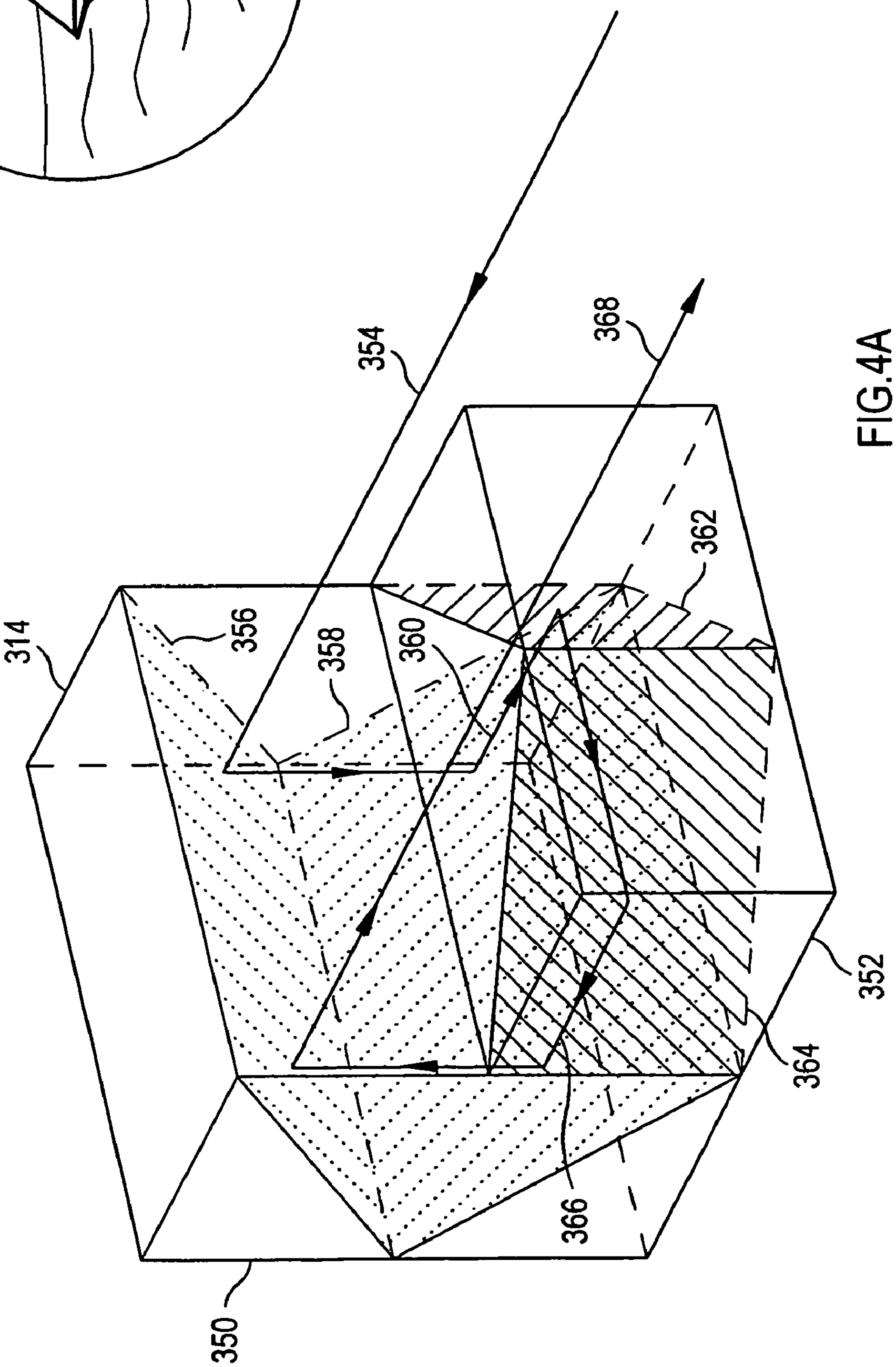
FIGS. 4A and 4B are diagrams of prisms implemented in the wavefront sensor of FIG. 2.

Turning to FIG. 4A, one embodiment for the trombone prism assembly 314 of FIG. 2 is shown effectively as a dual prism arrangement, including a first prism 350 and a second prism 352. As illustrated by a beam of light 354, the first prism 350 reflects the beam 354 off two faces 356 and 358 in succession, such that the resultant beam 360 is traveling in a direction or approximately in a direction parallel to the direction from which the beam 354 originated. The beam 360 impinges on the second prism 352, which reflects the beam 360 off two faces 362 and 364 in succession, resulting in a return beam 366. The return beam 366 is reflected off the faces 358 and 356 in succession, yielding the beam 368 traveling a path in the opposite direction or approximately oppositely in the direction parallel to the direction from which the beam 354 originated. A particularly advantageous aspect of this configuration is that the parallel or approximately parallel return path of the beam 368 is achieved irrespective of the angle at which the beam 354 enters the prism 314. This is because, in the vertical direction, the faces 356 and 358 maintain the vertical angle of deflection of the incoming beam 354, and the faces 362 and 364 maintain the horizontal angle of deflection. Although the focusing prism 314 is helpful for providing the beam from the laser diode 306 to the eye E, it is especially helpful on the return path, because the backscattered light returned from the eye E is not collimated like the beam from the laser diode 306 impinging on the eye E. Because the prism 314 returns the backscattered light from the eye E (that eventually will be sampled by the lenslet array 324) in a perpendicular path, it prevents or reduces the likelihood of error within the lenslet camera 312.

Figure 4B:
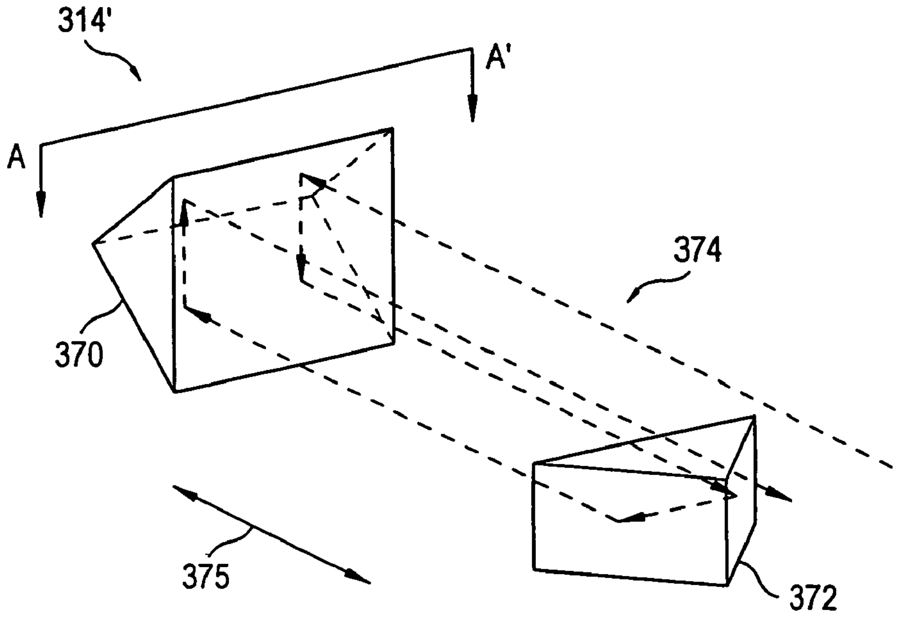

In FIG. 4B, another trombone-type optics 314' is shown that can be implemented for the prism 314 in FIG. 2 according to the invention. The optics 314' includes two prisms 370 and 372 in spaced-apart relation. The prisms 370 and 372 form a folded optical system that reflects six times both the light from the laser diode 306 traveling toward the eye E and the light backscattered from the retina of the eye E traveling toward the lenslet array 324 and the lenslet camera 312, in similarity to the surface reflections by the prism 314 shown in FIG. 4A. The six reflections are schematically illustrated in FIG. 4B as light 374. Although other configurations are possible, in practice, the lens 372 typically are fixed in position and the lens 370 is adjusted in position—shown by arrow 375 in FIG. 4B as one nonlimiting type of trombone movement—relative to the lens 372 to achieve optimal or near optimal focusing of the light passing through the lenslet array 324 to the lenslet camera 312. The variable spacing between the prisms 370 and 372 is preferably from about 5 mm to about 100 mm and their dimensions are preferably 40×40 mm and 20×40 mm, respectively, although other spacings and dimensions are possible.

Figure 4C:
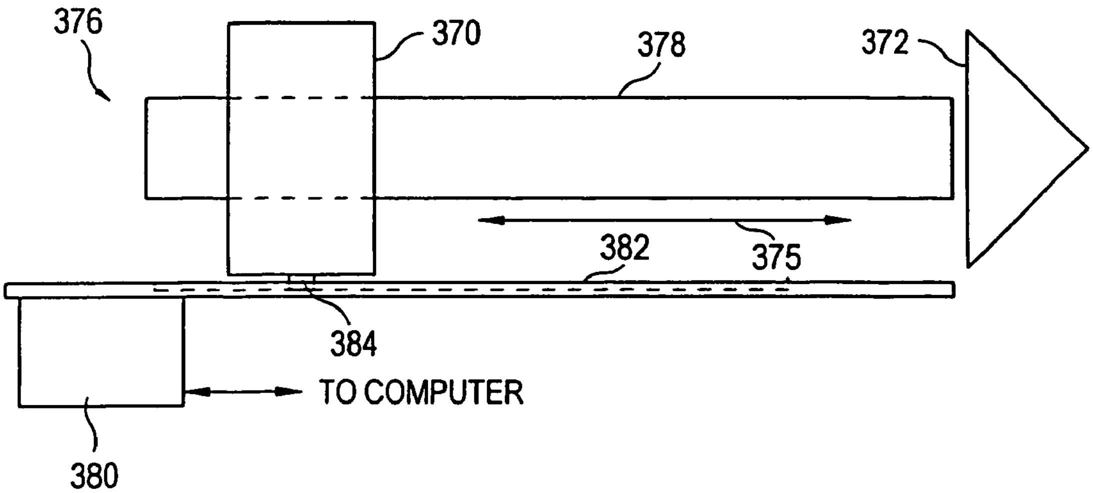
FIG. 4C is a diagram of a drive system for the prisms in FIG. 5B according to the invention.

The arrangement of the prisms 370 and 372 advantageously provides a reflected outgoing beam that is exactly or nearly exactly parallel to the incoming beam (i.e., whether to or from the eye E), even if the prism 370 is tilted during trombone movement. This potentially can reduce the cost of a slider or sliding mechanism that can be implemented to provide automated computer-controlled trombone movement, such as slider 376 shown in FIG. 4C, although an expensive or high quality slider, or a manual slider, could also be used. FIG. 4C is a view taken along A-A' if the trombone 314' in FIG. 4B were on the slider 376. In FIG. 4C, the slider 376 includes a slide or track 378 on which the prism 370 rides, for example, using a suitable bracket or holder of optical components, as will be appreciated by those skilled in the art. The slider 376 also includes a stepper motor 380 to drive the position of the prism 370 along the slide 378, an arm 382 to which the prism 370 is mechanically coupled by a coupler 384 (shown schematically in FIG. 4C) that is any suitable coupler, as also will be appreciated by those skilled in the art. As the stepper motor 380 is activated, it drives the position of the coupler 384 attached to the prism 370 along the arm 382 in either direction of the arrow 375. The direction and extent of the drive is determined according to the focusing requirements of the beam from the laser diode 306 impinging on the eye E, and those of the lenslet array 324 and the lenslet camera 312, as adjusted by the trombone 314'. Further, additional focusing optics could be attached to the prisms 370 or 372, such that the focusing optics also receive the benefit of the autoreflecting property of the prisms 370 and 372. For example, the focusing optics of the wavefront sensor, rather than being implemented as the lenses 326, could in large part be placed on the face of the prism 372. A variety of other drive mechanisms, prism configurations, or lens systems, including focus-adjusting lens systems, instead of the trombone 314' (or 314), or the slider 376, could be used, as will be appreciated by those skilled in the art. For example, another alternative optical system for the trombone 314' (or 314) could be a lens system having the capability of adding or removing lenses, each lens of which may or may not be related in optical power to the other lenses by some series or other optical power relationship. An example of such a lens system is a phoropter or a lens system similar thereto. With this type of lens system, the patient could see what improvement (e.g., for defocus and astigmatism) conventional vision-correcting techniques, such as conventional glasses or contacts could provide, and then see what could be provided by correction of other and higher order aberrations as a comparison.

Center Calculation for Wavefront Sensor Spot Locations

Figure 5B:
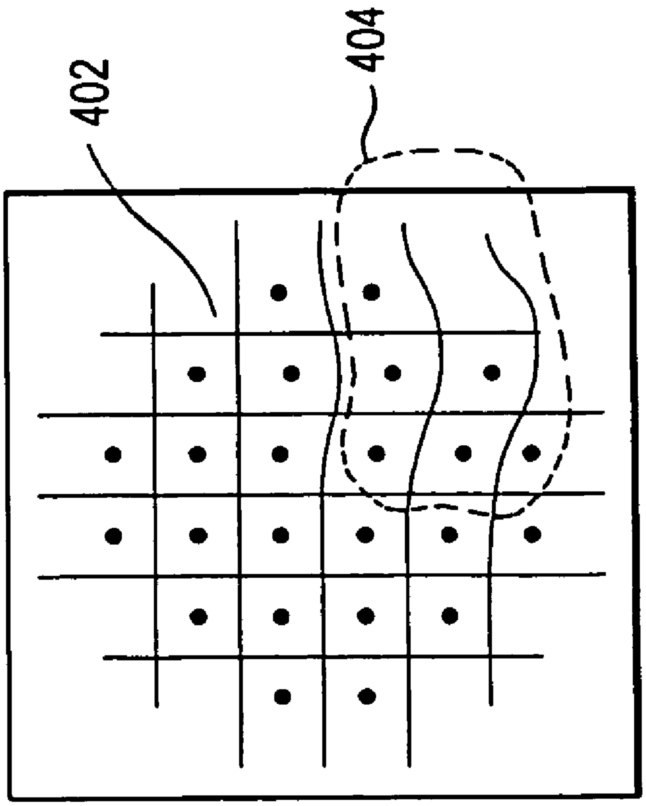
FIGS. 5A and 5B are diagrams representing typical data returned by the wavefront sensor of FIG. 2 according to the invention.
Figure 5A:
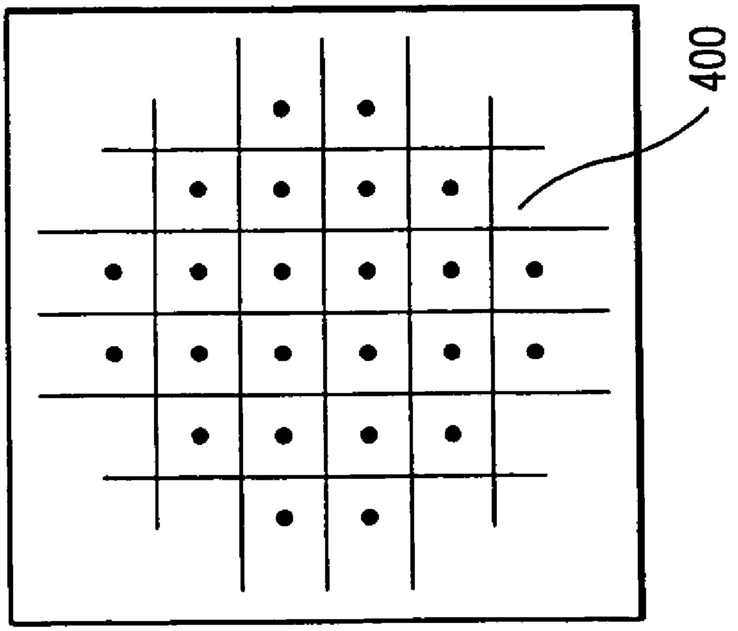
Figure 6:
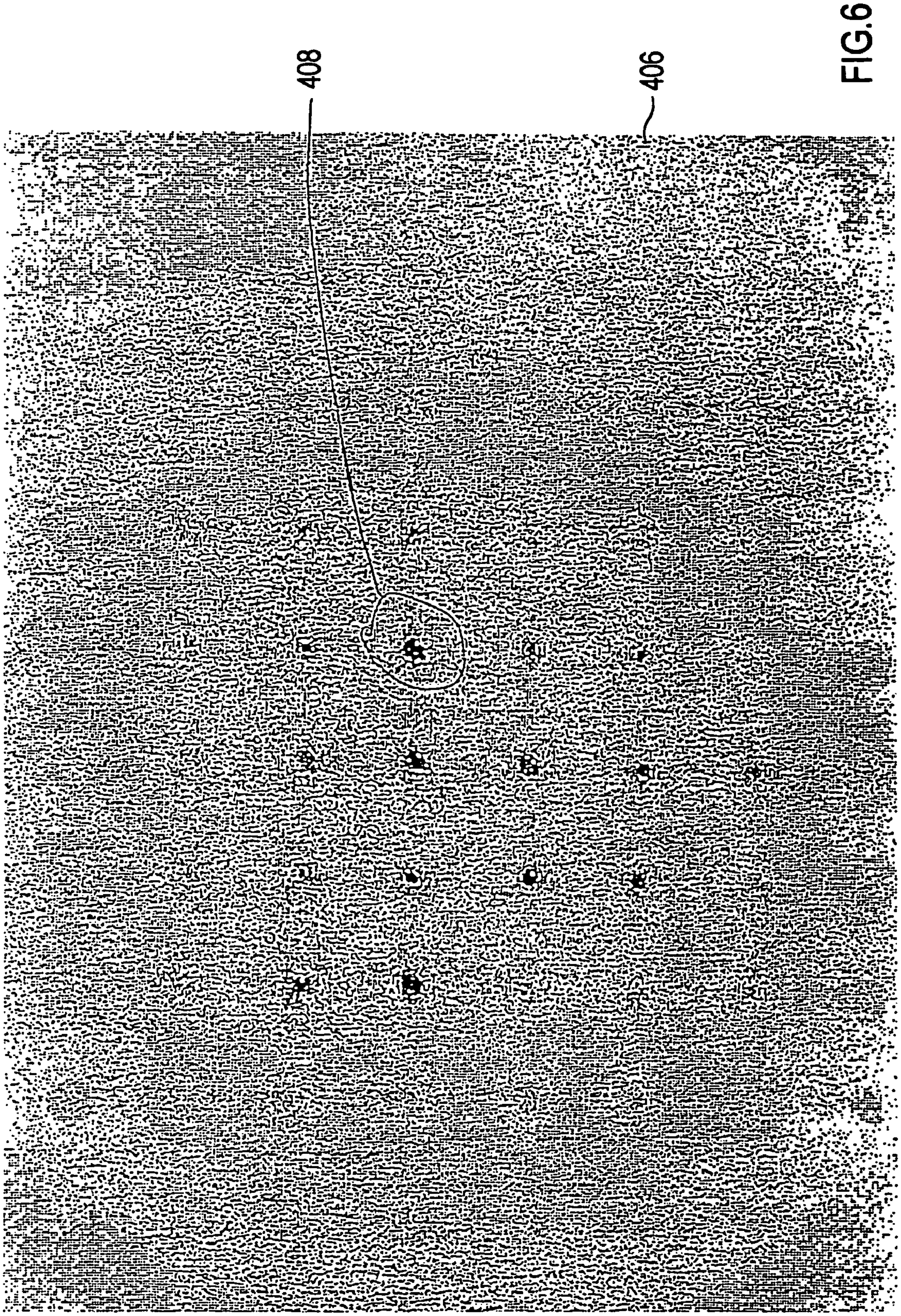
FIG. 6 is an image of actual data returned from a wavefront sensor as illustrated in FIG. 2.

Referring to FIGS. 5A, 5B, 6, 7A, and 7B, another feature of the wavefront sensor 300 is illustrated according to a feature of the invention. Referring also to FIG. 2, the lenslet array 324 of the lenslet camera 312 typically creates an array of spot images (or aerial images) on the sensor of the lenslet camera 312. As discussed in Williams, parameters or information related to the center points of these spots, such as the two-dimensional displacement of the center points from the ideal positions of the spots, are used in conjunction with a mathematical transformation, such as a fit with Zernike polynomials of various orders, to determine the wavefront aberrations associated with the eye E. FIG. 5A shows, for example, an array of spots 400 on the sensor that would be typical of a "perfect" eye in which the spots are not displaced from their ideal center points. FIG. 5B, on the other hand, shows an array of spots 402 that are displaced in a region 404, indicating the presence of wavefront aberrations of the eye. The aberrations are determined by analysis of the mathematical transformation, for example, by analysis of the Zernike polynomials used to fit the parameter data. The lines in FIGS. 5A and 5B are included merely to illustrate the deviation in the array of spots 402, and generally would not appear in the image in the lenslet camera 312. An actual (inverted or negative) image 406 from a lenslet camera like the lenslet camera 312 is shown in FIG. 6. The image 406 illustrates the type and quality of spots that would typically be observed with the lenslet camera 312.

As discussed above, the adjustment camera 323 (see FIG. 2) is intended to sharpen the light spot on the retina of the eye E, such that each spot like a spot 408 on the lenslet camera 312 is as focused as possible. Because such adjustment is only for low order effects, however, each resulting individual spot generally will not be a precisely sharpened point. As discussed in Williams, adaptive optics can be used in conjunction with the image developed so that a sharper "picture" of the spots is obtained with correction of aberrations. But in the wavefront sensor 300 of FIG. 2, such adaptive optics are not used, and the image 406 of the spots like the spot 408 may appear somewhat "smeared" due to the optical aberrations of the eye E. Referring again to FIGS. 5A and 5B, it is understood that the mathematical transformation used to determine the overall wavefront aberration of the eye uses information related to the particular points available in an array of spots, such as the arrays of spots 400 and 402. Therefore, apparent "smearing" of these spots like the spot 408 can prevent their center points (e.g., the centers of maximum weighted intensity) from precisely being located.

Figure 7B:
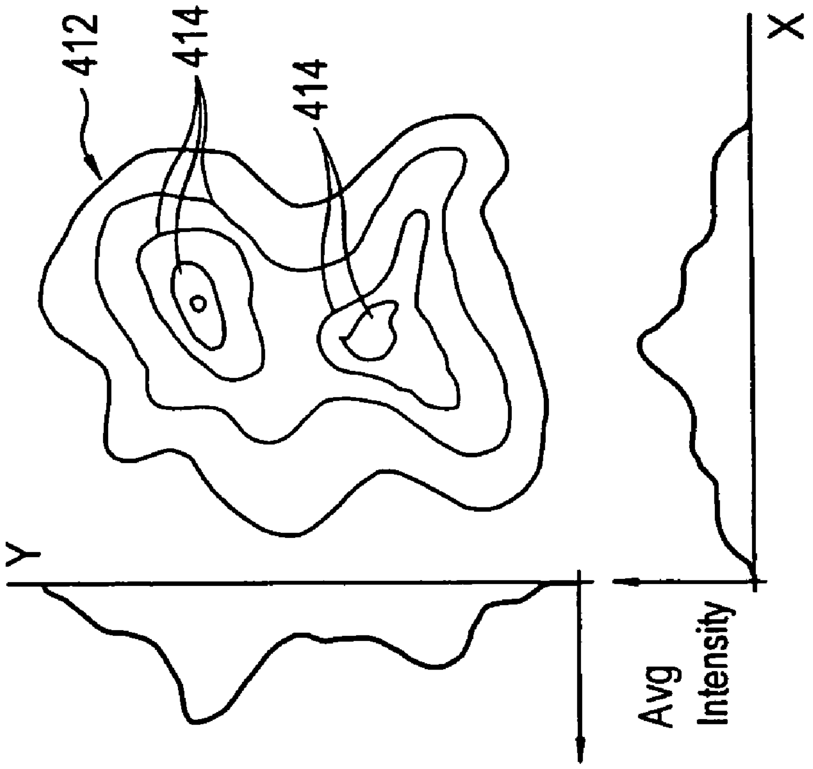
FIGS. 7A and 7B are representations of the blurred wavefront sensor data returned by a wavefront sensor, as well as the generation of a center of mass of the data points of the wavefront sensor.
Figure 7A:
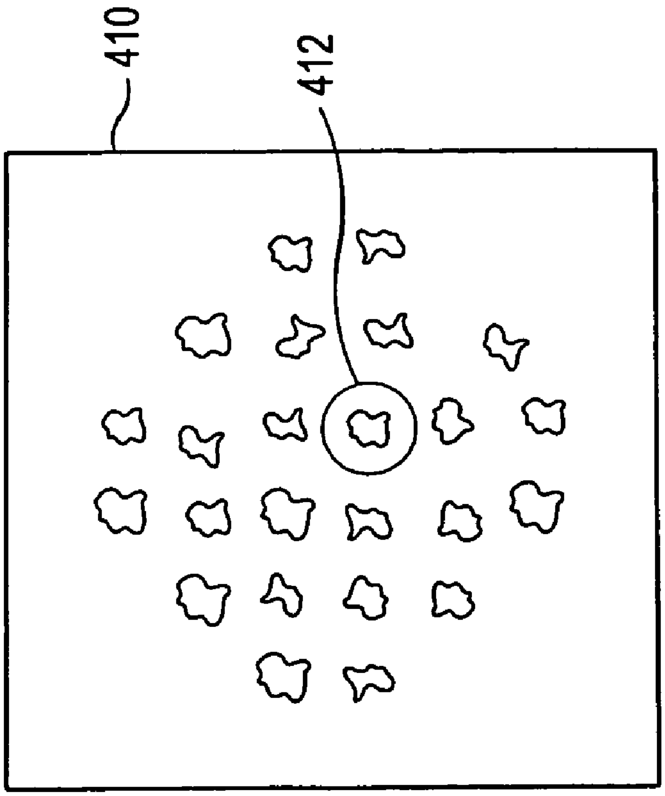

Turning to FIGS. 7A and 7B, diagrams illustrate a center of mass technique to determine the center point of each spot like the spot 408 of FIG. 6. Specifically, FIG. 7A shows an array 410 of "smeared" spots, such as a spot 412. A more detailed profile of the spot 412 is illustrated in FIG. 7B, which includes profile lines 414 that indicate an increase in intensity, in general, towards the center of the spot 412, much like equipotential lines or elevation contour plots. The increase in intensity correspondingly would be found in the digitized values of the sensor (e.g., CCD) in the lenslet camera 312, and can be seen as the darker areas in the spots of FIG. 6.

A number of techniques can be used to derive the center points for the various spots, according to embodiments of the invention. One technique employs a weighted intensity "center of mass" in the X and Y directions of a coordinate system, as illustrated in FIG. 7B, for which the respective center of masses for each spot are given by the following equations:

$$\bar{x} = \frac{\sum_i I_i x_i}{\sum_i I_i}$$

$$\bar{y} = \frac{\sum_i I_i y_i}{\sum_i I_i}$$

In these equations, $I_i$ is the intensity at a particular point. The intensity can be calculated in a number of ways, for example, as a threshold intensity, such that any pixel value greater than the threshold is assigned an intensity of 1 and any pixel value less than the threshold is assigned an intensity of 0. A weighted intensity that is simply the pixel intensity instead could be used. The intensity could be non-linearly weighted with higher intensity pixels having a greater than linearly proportional effect, such as by squaring the intensity value $I_i$. Other non-linear weightings could be used. In any case, it is possible to weight the intensity values $I_i$ in various ways to calculate the "centers" of the spots on the wavefront sensor.

Use of Centroid Spacing for Focus

Figure 8A:
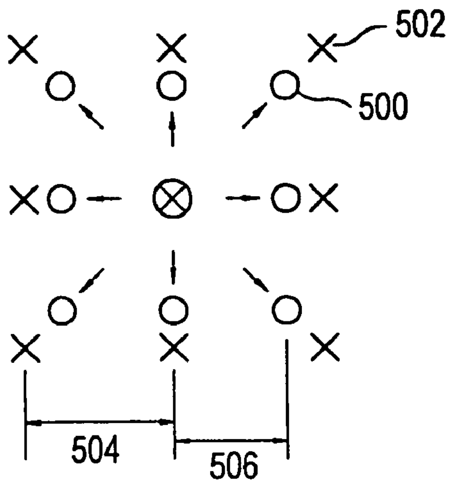
FIGS. 8A-8D are diagrams illustrating average centroid spacing.
Figure 8B:
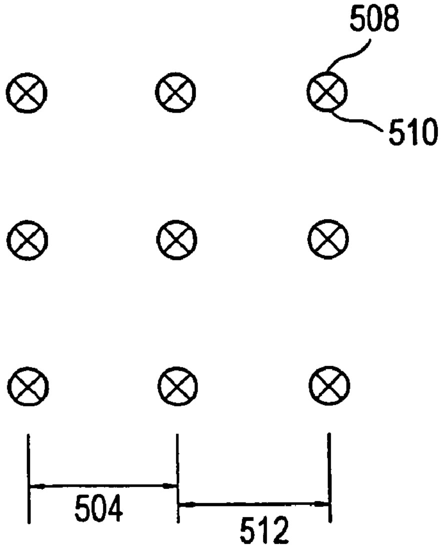
Figure 8C:
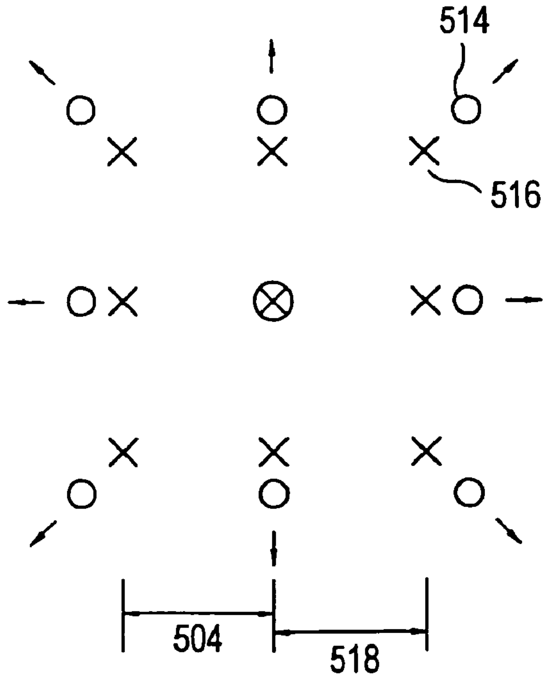

Instead of using the adjustment camera 323 to focus the wavefront sensor 300, it is possible to focus the wavefront sensor 300 employing the lenslet camera 312 based on centroid spacing. For a properly aligned eye E, when the wavefront sensor 300 has been properly focused the centroids appearing in the lenslet camera 312 have an average spacing that is equal to an ideal spacing. When the focus is slightly myopic, the centroids will have an average spacing that is less than the ideal spacing, and when hyperopic, greater than the ideal spacing. By starting with the trombone extended, and thus with the focus myopic, and then bringing the trombone in until the centroid spacing appearing in the lenslet camera 312 has an average spacing equal to the ideal spacing, defocus is then corrected. Preferably, one begins with the myopic focus because this corresponds to a fully relaxed lens of the eye E. The eye E can actually accommodate for a certain range of hyperopia, so by beginning with a myopic focus one does not induce such accommodation in the eye E. This concept is illustrated in FIGS. 8A-10D. Referring to FIG. 8A, shown are a number of actual centroids such as the centroid 500 appearing in the lenslet camera 312, which are compared with ideal centroids such as the centroid 502. Again, the ideal centroids such as centroid 502 are the centroids that would appear if a perfect eye was brought into focus employing the trombone prism 314. At this point, an ideal centroid spacing 504 is still greater than an average actual centroid spacing illustrated by centroid spacing 506. Assume, however, that the trombone prism 314 is slowly brought in until, as illustrated in FIG. 8B, actual centroids as illustrated by the centroid 508 have the same spacing as the theoretically ideal centroids as illustrated by the centroid 510. This is illustrated by a spacing 512 compared to the ideal spacing 504. At this point, the wavefront sensor 300 is in focus. Of note, in an actual eye E, the various centroids illustrated by the centroid 508 would not all be ideally aligned with the theoretical centroids such as the centroid 510 because of the other, higher order effects on the eye. However, if the average spacing of the centroids is equal to the ideal spacing, this indicates that the defocus has been compensated.

Figure 8D:
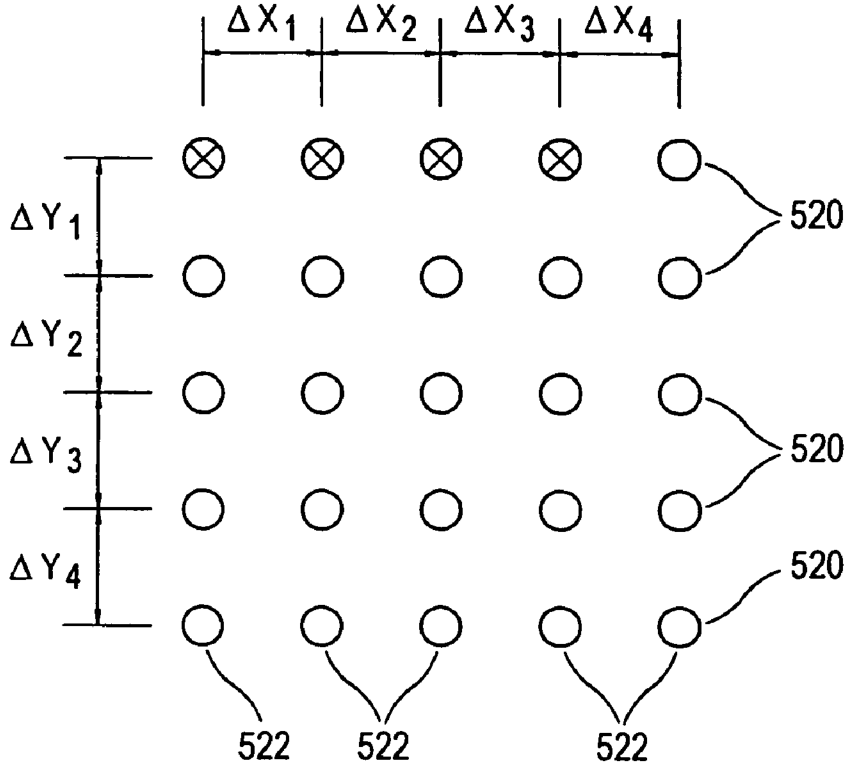

FIG. 8D illustrates one technique for determining overall centroid spacing. In this approach, a Y-axis "center" is determined for each row 520 of centroids and an X-axis "center" is determined for each column. This can be done using center of mass, weighted center of mass, or other techniques. Then, the $\Delta Y_n$ and $\Delta X_n$ spacing are summed, yielding an overall $\Delta Y$ and $\Delta X$. Of note, this process could again be weighted or other than a simple sum. Finally, the overall $\Delta Y$ is averaged with the overall $\Delta X$, yielding an average $\Delta$. This value is then used to determine when the system comes into focus.

Figure 9:
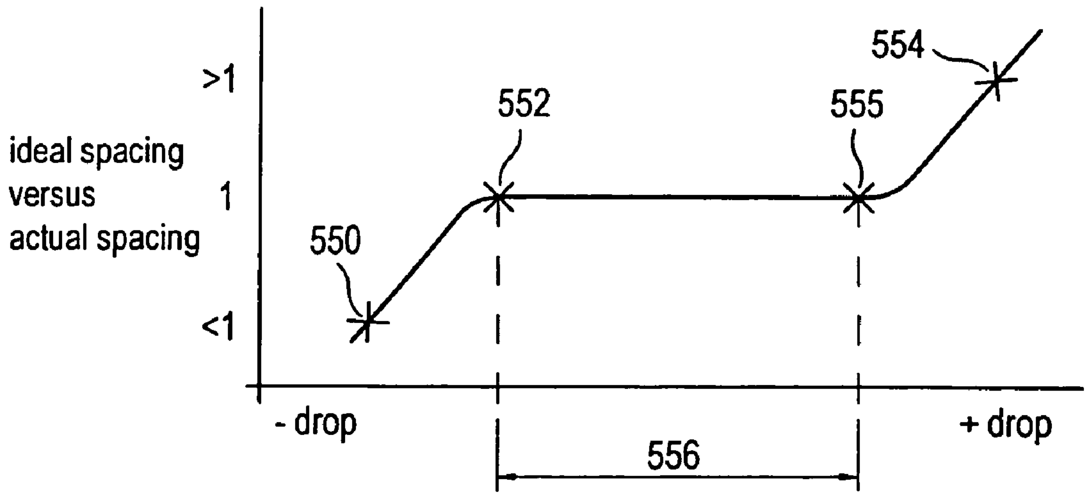
FIG. 9 is a graph of average centroid spacing versus refractive corrections.

Referring to FIG. 9, shown is the ideal spacing versus actual spacing compared to the wavefront sensor 300 focus in a graph. FIG. 8A corresponds to a point 550 on this graph, where the ideal spacing exceeds the actual spacing. FIG. 8B corresponds to a point 552, where the ideal spacing equals the actual spacing. A point 554 corresponds to a spacing illustrated in FIG. 8C, where a number of actual centroids such as a centroid 514 are continuing to expand away from a number of ideal centroids as indicated by a centroid 516. That is, an actual average centroid spacing 518 is now greater than the ideal centroid spacing 504. As illustrated in the graph of FIG. 9, the point 554 shows that as the trombone is brought further and further in, the focus becomes hyperopic.

As will be appreciated, if the trombone of the wavefront sensor 300 is brought in until the point 552 is reached, and thus the average theoretical centroid spacing 504 equals the average actual centroid spacing 512, the wavefront sensor 300 will be in focus. This allows the elimination of the adjustment camera 323 and focusing using the lenslet camera 312, but without requiring each individual centroid to be examined for the amount of "spread" in the centroid. That is, the centroid spacing, as opposed to sharpness is employed for focusing.

Preferably, this focusing technique is controlled by the control system of the wavefront sensor 300.

Determination of Accommodation Range

Figure 10A:
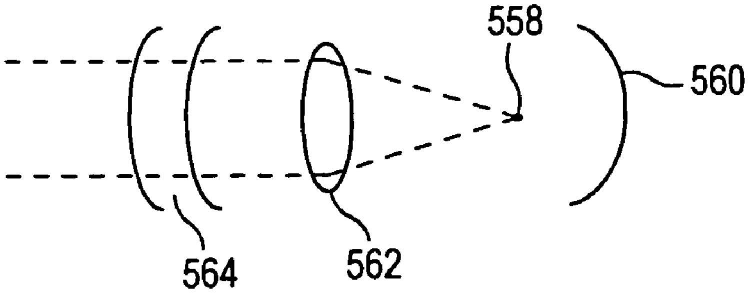
FIGS. 10A-10D are cutaway views of an eye illustrating focal points during accommodation.
Figure 10B:
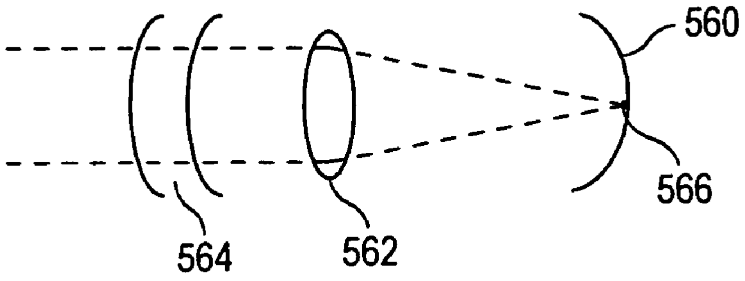
Figure 10C:
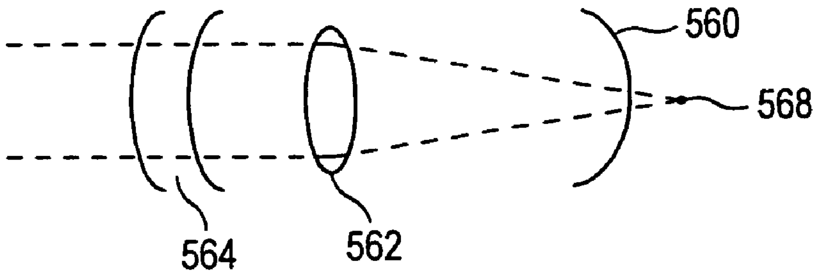
Figure 10D:
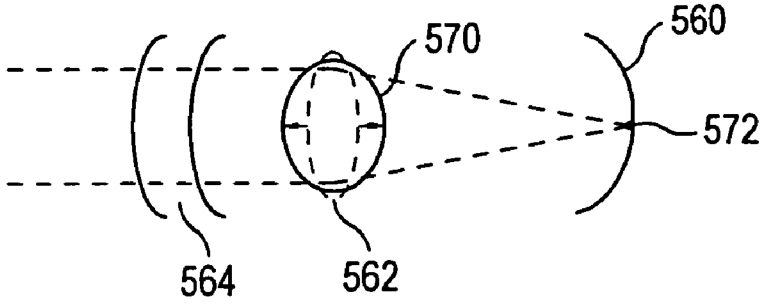

Referring to FIG. 9, it is seen that there is a range 556 over which the trombone can be moved in the wavefront sensor 300 and yet the centroid spacing stays on the average ideal and thus the eye E in focus. This is because the eye E can accommodate for a range, such as 2 to 4 diopters, by compressing the lens within the eye E. This is illustrated in FIGS. 10A-10D. In FIG. 10A, which would correspond to the point 550 in the graph of FIG. 9, a focal point 558 falls in front of a retina 560. This focal point 558 is the result of a relaxed lens 562 and a cornea 564. As the trombone of the wavefront sensor 300 is brought in, the focal point moves toward the retina 560, yielding in FIG. 10B a focal point 566, which falls upon the retina 560, and thus the eye is in focus. This corresponds to the point 552 in FIG. 9. As the trombone is brought further in, if the eye E did not accommodate, a focal point 568 in FIG. 10C would fall beyond the retina 560. But referring to FIG. 10D, instead the lens 562 accommodates, yielding a lens shape 570, and maintaining a focal point 572 upon the retina 560. This accounts for the range 556 in FIG. 9 over which the centroid spacing remains essentially constant. Once the range of accommodation of the accommodated lens 570 is reached, however, the focal point will again extend beyond the retina 560, yielding the point 554 in the graph of FIG. 9.

By monitoring the average spacing of the actual centroids, the wavefront sensor 300 can also therefore be used to determine the overall range of accommodation of the lens 562. By bringing the trombone slowly in and constantly monitoring the average spacing of the centroid, the range 556 is determined in FIG. 9. Essentially, once the eye is brought into focus, as the trombone is brought in increasing the dioptric power, the eye E accommodates by compressing the lens as illustrated by the lens 570. This continues until a point 555 is reach in FIG. 9, at which the lens can no longer compress and be accommodated, and the centroid spacing again begins to expand. By determining these two values, the overall range of eye accommodation can be evaluated.

As discussed above, the centroid spacing is an alternative to use of the adjustment camera 323 to focus the wavefront sensor. More generally, the centroid spacing is an alternative to bringing individual centroids into focus. But whatever focusing technique is used, the overall accommodation range can be determined using the foregoing technique.

Determination of the Changing Shape of a Lens When Relaxed and Accommodated

Figures 11, 12:
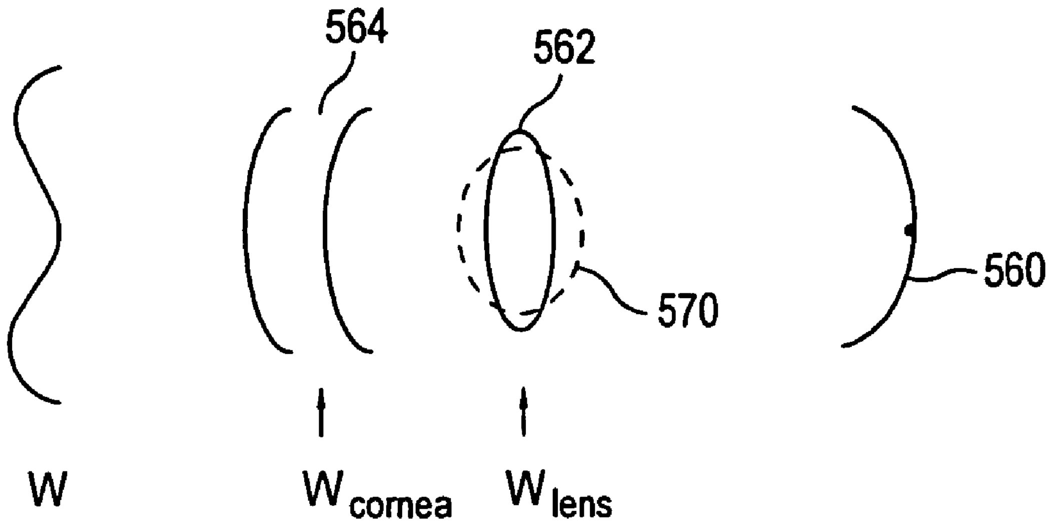
FIG. 11 is a cutaway view of an eye illustrating wavefront contribution by various components.
FIG. 12 shows equations for calculating the change of shape of a lens during accommodation.

The ability of the wavefront sensor 300 to force the eye to accommodate, and to monitor the centroids while it does so, can be employed to evaluate the change of the shape of the lens 562, as illustrated in FIG. 11 and the equations of FIG. 12. In FIG. 11, shown is the relaxed lens 562 and a fully accommodated lens 570. A wavefront W is determined by the lenslet camera 312, and this wavefront W is dependent both on a wavefront $W_{cornea}$ and a wavefront $W_{lens}$, both as illustrated in FIG. 11. It will be appreciated that the cornea wavefront $W_{cornea}$ stays essentially constant, whereas the lens wavefront $W_{lens}$ changes depending on the amount of accommodation in the lens 562.

Referring to FIG. 12, this is illustrated with reference to FIG. 9. When the point 552 is reached is the graph, a wavefront $W_\infty$ is captured. This wavefront $W_\infty$ is equal to the wavefront $W_{cornea}$ plus the wavefront $W_{lens}$, with the lens relaxed. The trombone is brought in until the point 555 is reached, at which point a fully accommodated wavefront, wavefront $W_0$ is captured, which again equals $W_{cornea}$ plus $W_{0lens}$. As indicated by the equations, the change in the wavefront of the lens, $\Delta W_{lens}$ is thus equal to $W_\infty$ minus $W_0$. But with the wavefront sensor, the shape change of the lens essentially becomes the shape change of the wavefront multiplied by a constant that dependent on the refractive characteristics of the lens relative to its surrounding fluid. Therefore, a shape change $\Delta$ shape is equal to k, a constant, times $\Delta W_{lens}$. While the change in wavefront $\Delta W_{lens}$ has been discussed solely as resulting from changes in the lens, the $\Delta W_{lens}$ is more properly the overall change in aberration of the eye during the accommodation process. For example, if accommodation affects the shape of the cornea, then that shape change will also contribute a component to $\Delta W_{lens}$.

In this way, the wavefront sensor can be used to evaluate the change of shape of lens (or more generally, the optics of the eye) as the eye accommodates.

CONCLUSION

The foregoing disclosure and description of the invention are illustrative and explanatory thereof, and various changes in the details of the illustrated apparatus and construction and method of operation may be made without departing from the spirit of the invention.

The invention claimed is:

1. A technique for focusing a wavefront sensor that creates aerial images that form centroids, comprising the steps of:

projecting a spot of light onto a retina;

dividing a reflected portion of the spot of light to form a plurality of aerial spots, each having a centroid;
monitoring spacing of the centroids;
adjusting the focus of the centroids on the sensor; and
determining when the sensor is in focus by determining when the average centroid spacing equals a focused sensor centroid spacing.

2. The method of claim 1 wherein the focus is adjusted from myopic to hyperopic.

3. The method of claim 2, further for determining accommodation range further comprising the steps of:
after determining when the sensor is in focus, continuing to adjust the focus until the centroid spacing again begins to change; and
determining the accommodation range as the difference between the focal power of the sensor when the centroid spacing equals the focused sensor centroid spacing and the focal power when the centroid spacing again began to change.

4. The method of claim 3, further for determining the change of shape of the lens of an eye over its accommodation range, further comprising the steps of:
capturing a wavefront when the sensor goes into focus;
capturing a wavefront when the wavefront sensor again goes out of focus; and
determining the difference between the two captured wavefronts.

5. The method of claim 4, further comprising the step of:
determining the change of shape of optical components of the eye to be the difference in the two wave fronts multiplied by a constant.

6. A wavefront sensor, comprising:
a lenslet array adapted to receive an image of a light spot on a retina of the eye and for creating aerial images of the light spot;
a sensor adapted to receive the aerial images from the lenslet array;
focusing optics adapted to adjust the focus of the wavefront sensor;
a processor adapted to receive signals from the sensor corresponding to the aerial images and to determine the wave aberrations from the signals; and
a focus control system adapted to adjust the focus of the wavefront sensor by performing the computer implemented steps of:
monitoring spacing of the aerial images;
adjusting the focus of the centroids on the sensor; and
determining when the sensor is in focus by determining when the average spacing of the aerial images equals a focused sensor aerial image spacing.

7. The wavefront sensor of claim 6, wherein the focus is adjusted from myopic to hyperopic.

8. The wavefront sensor of claim 7, the sensor further determining accommodation range, the focus control system further performing the computer implemented steps of:
after determining when the sensor is in focus;
continuing to adjust the focus until the centroid spacing again begins to change; and
determining the accommodation range as the difference between the focal power of the sensor when the centroid spacing equals the focused sensor centroid spacing and the focal power when the centroid spacing again began to change.

9. The wavefront sensor of claim 8, the processor further determining the change of shape of the lens of an eye over its accommodation range, the processor and focus control system further performing the computer implemented steps of:
capturing a wavefront when the sensor goes into focus;
capturing a wavefront when the wavefront sensor again goes out of focus; and
determining the different between the two captures wavefronts.

10. The wavefront sensor of claim 6, wherein the focus control system employs the processor.

11. A wavefront sensor, comprising:
a lenslet array adapted to receive an image of a light spot on a retina of the eye and for creating aerial images of the light spot;
a sensor adapted to receive the aerial images from the lenslet array; focusing optics that adjust the focus of the wavefront sensor;
a processor adapted to receive signals from the sensor corresponding to the aerial images and to determine the wave aberrations from the signals; and
a focus control system that adjusts the focus of the wavefront sensor by performing the computer implemented steps of:
determining when the wavefront sensor goes into focus;
adjusting the wavefront sensor until the wavefront sensor begins to go out of focus; and
determining the accommodation range as the difference between the focal power of the sensor when the sensor goes into focus and the focal power of the sensor when the sensor begins to go out of focus.

12. The wavefront sensor of claim 11, the processor further adapted to determine the change of shape of the lens of an eye over its accommodation range, the processor and focus control system further performing the computer implemented steps of:
capturing a wavefront when the sensor goes into focus;
capturing a wavefront when the wavefront sensor again goes out of focus; and
determining the different between the two captures wavefronts.

* * * * *